United States Patent [19]
Cook et al.

[11] Patent Number: 5,628,044
[45] Date of Patent: May 6, 1997

[54] PURE IRON-ZINC INTERMETALLIC GALVANNEAL CALIBRATION STANDARDS

[75] Inventors: Desmond C. Cook, Virginia Beach; Richard G. Grant, Blacksburg; Patricia S. Cook, Virginia Beach, all of Va.

[73] Assignee: Old Dominion University, Norfolk, Va.

[21] Appl. No.: 459,167

[22] Filed: Jun. 2, 1995

[51] Int. Cl.⁶ .................................. C22C 1/04; B22F 3/24
[52] U.S. Cl. .................... 419/3; 419/28; 419/29; 419/38; 419/46; 419/54; 419/55; 75/245; 75/246; 75/950
[58] Field of Search ........................ 419/3, 28, 29, 419/38, 46, 54, 55; 75/245, 246, 950

[56] References Cited

U.S. PATENT DOCUMENTS

| | | | |
|---|---|---|---|
| 4,540,472 | 9/1985 | Johnson et al. | 204/28 |
| 4,543,300 | 9/1985 | Hara et al. | 428/610 |
| 4,578,158 | 3/1986 | Kanamura et al. | 204/44.2 |
| 5,316,652 | 5/1994 | Sagiyama et al. | 205/177 |

FOREIGN PATENT DOCUMENTS 646783  4/1995  Germany ............... G01N 21/62

OTHER PUBLICATIONS

Commandeur et al., EP646783, Germany Apr. 5, 1995 Chem Abstact.

Primary Examiner—Charles T. Jordan
Assistant Examiner—Daniel Jenkins
Attorney, Agent, or Firm—Whitham, Curtis, Whitham & McGinn

[57] ABSTRACT

High purity iron-zinc intermetallic calibration standards are produced using a slow diffusion technique. The alloys are pure to greater than 99.5 wt % and are homogenous to greater than 98%. The alloys can be used to calibrate instrumentation used to monitor and measure galvanneal and galvanized coatings. The alloy calibration standards for each of the iron-zinc phases allows instrumentation correction factors to be determined for iron-zinc coating analysis.

14 Claims, 5 Drawing Sheets

PURE IRON-ZINC INTERMETALLIC GALVANNEAL CALIBRATION STANDARDS

DESCRIPTION

BACKGROUND OF THE INVENTION

1. Field of the Invention

The invention is generally directed to high purity iron-zinc alloys and a method of preparing the alloys. More particularly, the invention is directed to the preparation of iron-zinc alloys of calibration standard quality.

2. Description of the Prior Art

The demand to improve the corrosion resistance of steel sheet, particularly for use within the automotive industry, has led to a dramatic increase in the use of coated steels in place of ordinary cold-rolled sheet steel. Consequently, industrial interest in the processing of zinc alloy coatings has risen over the past decade. Hot-dip galvanized and galvannealed sheet steel are two products in use today. These processes involve the use of zinc and zinc-alloy coatings to protect the steel through the sacrificial or galvanic mechanism. They are an economic way to apply the zinc, and today's continuous coating lines are capable of producing materials having well controlled coating thickness and uniformity.

Galvanneal steel differs from galvanized steel in that it results from the post annealing of the zinc-coated steel sheet, thereby allowing the interdiffusion of the iron and zinc to form an iron-zinc intermetallic coating. The iron content in the coating depends primarily on the anneal temperature and time. Within this alloy coating, the four different iron-zinc phases, Zeta, Delta, Gamma-1, and Gamma, may be present. In order to manufacture the most advantageous coating, it is important to identify which phases form during the galvannealing process, to understand the properties of each phase, and to know how to control the formation of any particular phase or phases in order to obtain optimal material performance. Positive identification of each phase and the fraction present in a galvanneal coating is very difficult. The primary cause of this difficulty is the lack of high quality data on the crystal structure and the related microstructure of the separate iron-zinc phases.

Although several publications discuss the preparation of some iron-zinc intermetallics (see, Baskin et al., Z. Metallkde, 68, 359 (1977), and Gellings et al., Z. Metallkde, 70, 312 (1979)), to date, none report on the preparation of the alloys having high purity and homogeneity. It would be advantageous to produce very pure and homogenous iron-zinc alloys which are useful as instrument calibration standards, such that galvanneal coatings can be more effectively evaluated.

SUMMARY OF THE INVENTION

It is an object of this invention to provide high purity iron-zinc alloys useful as calibration standards for instrumentation used to analyze galvanneal coatings.

According to the invention, a homogenous mixture of precise quantities of iron and zinc powders is compressed into a dense article or tablet such that the iron and zinc are in close proximity. The size and purity of the iron and zinc play important roles in the final product. To promote homogenous diffusion, the materials should be very fine powders (<100 µm) and the materials should be thoroughly mixed prior to being pressed into dense articles or tablets. Both the iron and the zinc should be as pure as possible (e.g., purity of at least 98 wt %). The high purity of the powderized iron and zinc starting materials will prevent or reduce the production of iron carbide, nitride, or oxides. Because the melting temperatures of iron and zinc are very different, 1578° C. and 420° C., respectively, a low temperature (e.g., <1000° C., and preferably <700° C.) sintering process is used to cause the zinc to diffuse into the iron, and care is taken to prevent zinc loss by evaporation. To assist in minimizing the time and temperature required for interdiffusion, it is advantageous to use extremely fine iron particles (e.g., less than 20 µm and preferably less than 10 µm or 5 µm). By using extremely fine iron particles the distance required for zinc diffusion to produce a homogenous alloy is decreased. After sintering, the intermetallic is powderized to remix before annealing, and the powder is then annealed to produce the iron-zinc alloy. The iron-zinc alloy is then characterized for the actual Fe and Zn concentrations and homogeneity, and is then useful as a calibration standard.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

In order to accurately study the microstructural properties of the iron-zinc intermetallic alloys, it is necessary to be able to to produce high quality samples which are representative of any chosen point on the Fe-Zn binary phase diagram. Each sample needs to be homogenous and have an iron content measured to an accuracy of approximately ½ wt %. At the same time, the samples need to be very pure, containing substantially no substitutional or interstitial elements which would effect the crystal structure and general microstructural properties.

This invention is directed to the production of very pure and homogenous iron-zinc alloys which ar suitable as instrument calibration standards. These samples will be useful in the analysis of galvanneal coatings.

Figure 1:
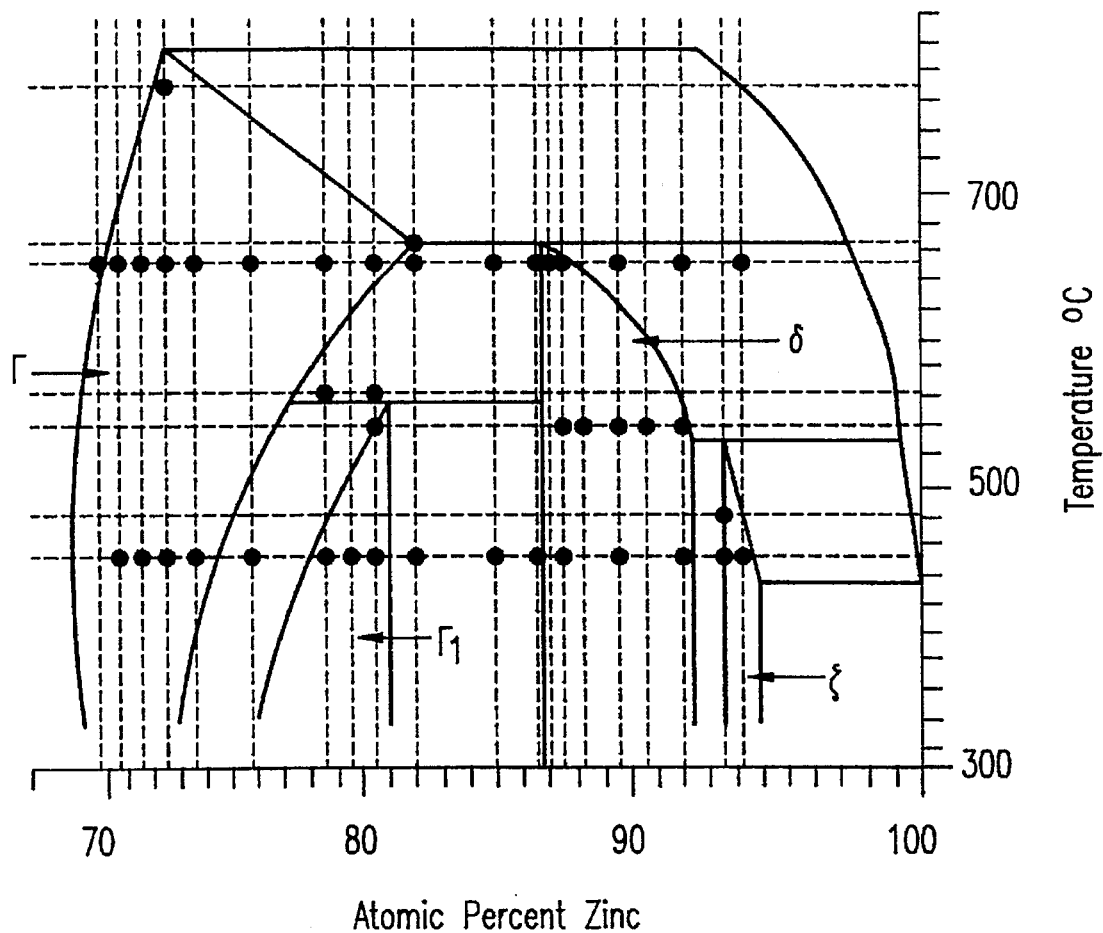
FIG. 1 is an iron-zinc binary phase diagram showing the high zinc concentration end of the iron-zinc phase diagram and showing the Gamma, Gamma-1, Delta, and Zeta phases.

FIG. 1 is an iron-zinc binary phase diagram, and it shows four intermetallic phases at the low iron end. They are Gamma, $Fe_3Zn_{10}$ (15.8–27.7 wt % Fe), Gamma-1, $Fe_5Zn_{21}$ (16.6–21.2 wt % Fe), Delta ($\delta$), $FeZn_{10}$ (7.0–11.5 wt % Fe), and Zeta ($\zeta$), (5.2–6.1 wt % Fe). This invention contemplates the production of a series of calibration standards having varying concentrations of iron and zinc within each of the four phases identified above.

The starting materials are very important to the production of satisfactory iron-zinc alloy calibration standards. It is important to prevent iron carbide, nitride and oxide precipitates from forming in the iron-zinc alloy, since these precipitates will reduce the iron fraction and uniformity in each phase. The purity of the materials used will influence the tendency of these precipitates to form in the iron-zinc alloy, thus, within the practice of this invention, the iron and the zinc starting materials should be at least 97 wt % pure. However, superior results are achieved with materials that are of greater purity, and it is preferred that the iron material be at least 98 wt % pure and that the zinc material be at least 99 wt % pure. In addition, to promote homogenous diffusion, the iron and zinc starting materials should both be very fine powders (<20 µm for iron and <100 µm for zinc) which are thoroughly mixed and pressed into dense articles or tablets.

Many iron and zinc powders are commercially available with different purity and particle size. Generally, the smaller the particle size, the lower the purity. In the practice of this invention, the selection of iron and zinc powders is made using different criteria. Since the zinc diffuses into the iron during alloy formation, choosing iron powder having small particle size (<20 µm and most preferably less than 5–10 µm) is important even at the expense of the powder purity. Use of fine iron powders containing more than 0.1 wt % of carbon or oxygen should be avoided due to the known formation of iron carbides and oxides. The iron powder should not contain more than 0.1 wt % carbon, nitrogen or oxygen, since these impurities will cause the formation of iron carbide and iron oxide precipitates that will reduce the iron fraction and uniformity in each phase.

Superior results were achieved using an electrolytic iron powder that had a particle size of less than 4 µm. During sample sintering, zinc can easily diffuse through this distance. As the iron particle size increases, the sintering time and temperature conditions will need to increase. Thus, using iron particles of less than 5–10 µm is most preferred. Above 20 µm, the ability to obtain homogenous iron-zinc alloys is compromised, thus, within the practice of this invention the iron powder should be no larger than 20 µm. The electrolytic iron powder used to prepare various calibration standards discussed below had a purity of only 98.2 wt % pure; however, it had an appreciable amount of hydrogen (1.5 wt %) which made up the majority of the impurity elements present. As discussed above, the electrolytic iron powder had a very low fraction of carbon and nitrogen in the powder (0.025 wt %).

The particle size of the zinc powder is not as important, since its diffusion is high for alloys prepared above 420° C. In the calibration standards that were prepared, as discussed below, the zinc powder had a purity of 99.9% and a particle size of 20 µm.

In preparing the calibration standards, the iron and zinc powders were purchased in sealed containers, and, once opened, were stored in an evacuated container to prevent oxidation and moisture uptake. Similar precautions should be taken within the practice of this invention, since, as discussed above, iron oxide or the like present in the starting material can form iron oxide precipitates which reduce the iron fraction and uniformity within each phase.

The melting temperatures of iron and zinc are very different. Specifically, iron has a melting temperature of 1578° C., while zinc has a melting temperature of 420° C. Therefore, when sintering iron and zinc together, care must be taken to prevent zinc loss by evaporation as the sintering temperature is increased.

In order to minimize zinc loss, it is recommended that calibration samples be prepared in accordance with the iron-zinc binary phase diagram shown in FIG. 1, whereby the iron-zinc mixture is not heated above the temperature defining the selected point on the phase diagram. That is, the sintering temperature is selected according to the iron-zinc fraction targeted on the phase diagram. For example, with reference to FIG. 1 if a 10% Fe $\delta$ phase Fe-Zn alloy calibration standard were desired, the sintering temperature should not exceed approximately 600° C. In all cases, the alloys should not be sintered above 1000° C. and are preferably made using sintering temperatures less than 800° C. Of importance when producing samples at temperatures less than 800° C., is to sinter for sufficiently long times to obtain homogeneity. For example, it is recommended that the samples should be sintered 6 hrs to 10 days, and optimum results have been achieved when sintering samples on the order of 4–10 days. Using this technique, identical iron-zinc mixtures have been sintered at different temperatures to allow the production of samples within one phase and to produce samples spanning several different phases, as is the case for the gamma and gamma-1 phases containing 17–20 wt % iron, yet have the same iron fraction. The time of heating does not have an effect on obtaining gamma phase versus gamma-1 phase; however, the temperature does have an effect, wherein lower temperatures (e.g. <560° C.) can be used to preferentially produce gamma-1.

Samples can be prepared in a wide variety of sizes depending on the amount of starting material used and the press used for compacting the sample prior to sintering. For exemplary purposes only, Example I sets forth the procedures used for sintering and annealing suitable, calibration standard quality samples; however, it should be understood that varying lo amounts of starting materials, heating cycles, heating equipment, and the like, can be varied widely within the practice of this invention.

EXAMPLE 1

Stoichiometric amounts of iron and zinc, 20–30 grams total, were carefully weighed and then encapsulated and then thoroughly mixed. All masses were weighed to an accuracy of 0.0001 grams. Mixing was achieved by axial sample rotation. A small quantity of each sample, 1–1.5 grams, was placed into a ½ press tool and subjected to 50 tons per square inch (tsi) to form an article or tablet approximately 1–2 mm thick. The size and shape of the pressed article can be varied at the discretion of the manufacturer. Best results have been achieved with cylindrical pressed articles that are 2 mm thick. The press procedure used produced samples with pressed densities of greater than 6.5 g/cm$^3$ which is close to the range of the iron-zinc alloy densities, 7.1–7.4 g/cm$^3$, for the four Fe-Zn phases. Other pressures and pressing procedures can be used within the practices of this invention, however, it is important that the homogenous mixture of Fe and Zn particles be subjected to a compressing operation to enhance interdiffusion of the Fe and Zn (particles are brought close together to help diffusion). Preferably, the compressing operation will be chosen to achieve a density in excess of 6 g/cm$^3$.

The articles or tablets produced during the compressing operation are then subjected to sintering. Suitable sintering results have been achieved by placing tablets into a sealed, evacuated, quartz tube, and then heating the quartz tube in an oven or furnace. Other sintering procedures may also be used. The Fe-Zn alloys of this invention were prepared by placing at least two tablets of the same mixture, and up to eleven different mixtures into a 12 cm long, 1.5 cm inside diameter, evacuated, quartz tube. Each tablet was separated by a small quartz disc, 1 mm thick and 12 mm in diameter, to prevent the tablets from touching. The samples were then sintered in a computer controlled furnace for varying times and temperatures depending on the desired sample. Care was taken to ensure that the evacuated quartz tube was completely inside the furnace, thereby allowing the entire tube to reach a uniform temperature. As discussed above, the sintering temperature was determined from the phase diagram for the particular phase required. In order minimize thermal stress within the pressed tablet, and to stop zinc loss, the temperature was increased slowly over a period of two hours until the final sintering temperature was reached.

Following sintering for 4–10 days, the samples were quenched in liquid nitrogen to preserve the microstructural properties present at the particular sintering temperature. Within the practice of this invention, it is recommended that sintering be performed for 6 hrs to 10 days to achieve homogenous Fe-Zn alloys. At the expiration of the sintering procedure, the samples should be cooled by quenching. Slow cooling can result in mixed phases or inhomogeneous samples.

After sintering, the tablets were removed from the quartz tube and crushed finely to between 1–10 μm. Powderizing the sintered tablet serves the function of remixing the powder before annealing to relieve sample strain. Powderizing the sintered sample can be achieved by using a mortar and pestle, or other suitable means. Each powder sample was individually encapsulated in another evacuated quartz tube and annealed at the same temperature and for the same time as the original sinter. Each sample was annealed separately during this stage of production. Annealing is performed to assure homogeneity and relieve residual strain in the powder particles due to pressing. The same temperature is used to maintain uniformity of sample preparation since a fraction of additional diffusion can occur.

With reference to FIG. 1, the datapoints on the iron-zinc binary phase diagram indicate twenty eight pure phase alloys produced at sintering temperatures of 450° C., 540° C., and 650° C., according to the techniques described above. Several other pure and mixed phase samples were also produced at the positions shown.

Example 2 describes the composition analysis of the samples produced according to the procedures of Example 1.

EXAMPLE 2

In the production of Fe-Zn calibration standards, the alloys produced according to the process discussed in Example 1, should be subjected to chemical analysis to determine the Fe concentration to less than 0.5 wt % accuracy. Electron microprobe analysis and scanning transmission electron microscope measurements should be performed to determine homogeneity. Greater than 99% homogeneity is preferred. Mössbauer analysis must also be performed to confirm the correct phase formed.

The chemical composition of all samples produced according to the technique of Example 1 was determined by Induction Coupled Plasma (ICP) spectroscopy, and wet chemical analysis. Additionally, sample homogeneity was determined with an electron microprobe and a scanning transmission electron microscope. The chemical analyses were performed on the pure iron and zinc powders, the mixed unsintered powders and the final sintered and annealed alloys. Once the composition and homogeneity was determined, the samples were microstructurally analyzed using X-ray diffraction, Mössbauer spectroscopy and Raman spectroscopy.

The Induction Coupled Plasma Spectroscopy, Wet Chemical Titration, Electron Microprobe, and Scanning Transmission Electron Microscopy results for the samples prepared according to Example 1 are discussed in connection with sections a-d of this Example 2.

a. Induction Coupled Plasma Spectroscopy

ICP analysis was performed at each stage of the sample preparation in order to monitor any change in the zinc concentration. An ICP Spectrometer with a standard plasma minitorch operating under argon gas was used for the studies. Absolute atomic concentrations of iron and zinc were determined using a commercial, custom-made multi-element standard containing 100 mg/l of each of iron and zinc in 2% $HNO_3$. Additional calibration standards were then produced with the iron and zinc powders, as described above in Example 1. A known mass of sample, approximately 100 mg, was dissolved in concentrated nitric acid by heating to approximately 100° C. in a fume hood for thirty minutes. A watch glass was placed over the beaker to prevent solution evaporation. Following cooling, the solution was diluted to 2 liters in a volummetric flask using highly purified water. The total atomic concentration was maintained at about 50 ppm so as not to exceed the upper saturation limit of the ICP spectrometer. The analysis was performed by setting the spectrometer on the 213.856 nm and 202.551 nm emission lines of zinc and the 259.94 nm and 273.955 nm emission lines of iron. The number of iron and zinc atoms per unit volume were measured at the original solution concentrations and also using dilutions of 1:1 and 1:9. This procedure minimizes errors due to background counting.

Figure 2A:
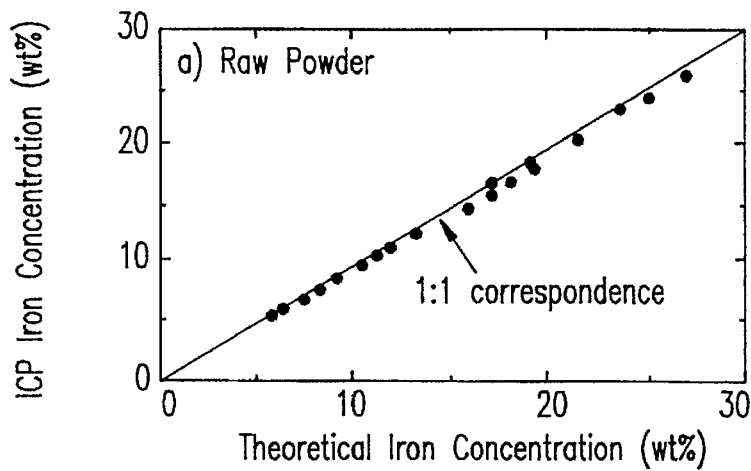
FIGS. 2a–2b are graphs plotting the measured iron concentration for mixed powders and fully sintered alloys, respectively, using induction coupled plasma spectroscopy versus the expected iron concentration from the initial masses of iron and zinc before the metals were mixed.
Figure 2B:
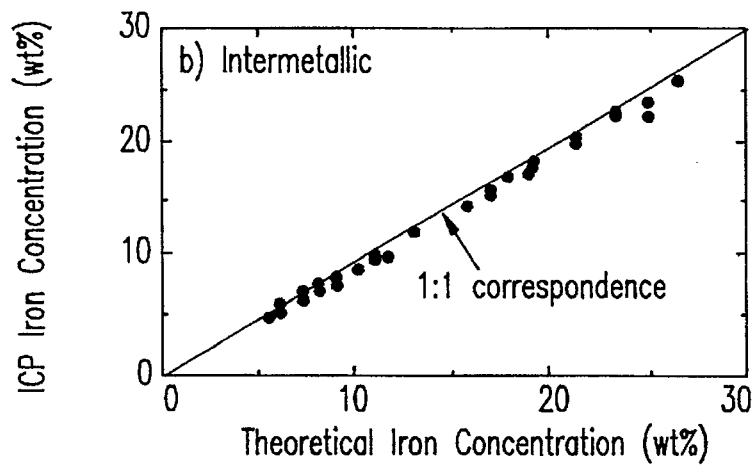
Figure 3A:
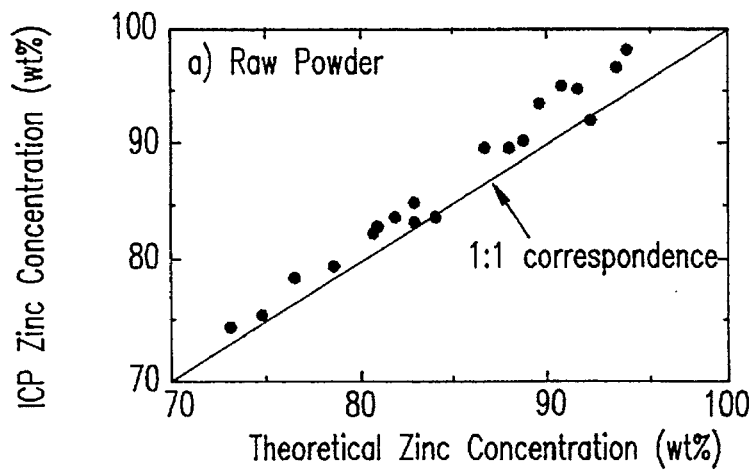
FIG. 3a–3b are graphs corresponding to FIGS. 2a–2b which plot the measured zinc concentration for mixed powders and fully sintered alloys, respectively, using induction coupled plasma spectroscopy versus the expected zinc concentration from the initial masses of iron and zinc before the metals were mixed.
Figure 3B:
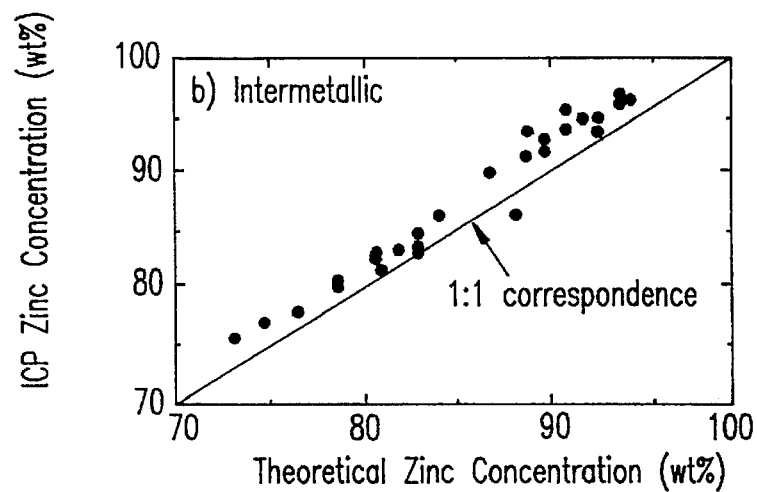

The unmixed and mixed powders as well as the sintered iron-zinc intermetallics were analyzed by ICP. FIGS. 2a and 2b indicate the measured fraction of iron in the mixed powders and the fully sintered alloys plotted against that which is expected from the initial masses of iron and zinc before the metals were mixed. FIGS. 3a and 3b show the corresponding plots of the ICP data for the fraction of zinc in each mixed powder and alloy. For each figure, the iron or zinc fraction is an average weight concentration in parts per million (ppm) at the two different iron or zinc absorption wavelengths and at three solution concentrations. On each graph is a solid line showing the 1:1 correspondence if the measured ICP wt % was to agree with the expected wt % in the original mix before sintering. As can be seen from the figures, the fraction of iron measured in the unsintered mixed powders and the fully sintered is less than expected. Furthermore, FIGS. 3a and 3b indicate that the scatter in the zinc data is much greater than that for the iron. From this data it could be incorrectly concluded that the difference is due to loss of iron during the sintering and annealing processes and that the alloys are deficient in iron. However, in general, a loss of zinc rather than iron would be expected from the heating process.

Figure 2C:
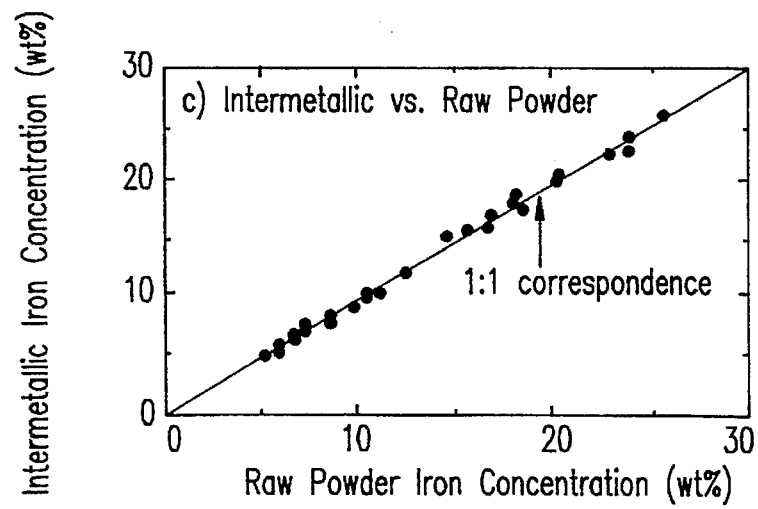
FIG. 2c is a graph comparing the measured iron concentration determined using induction coupled plasma spectroscopy for intermetallics versus raw powders.
Figure 3C:
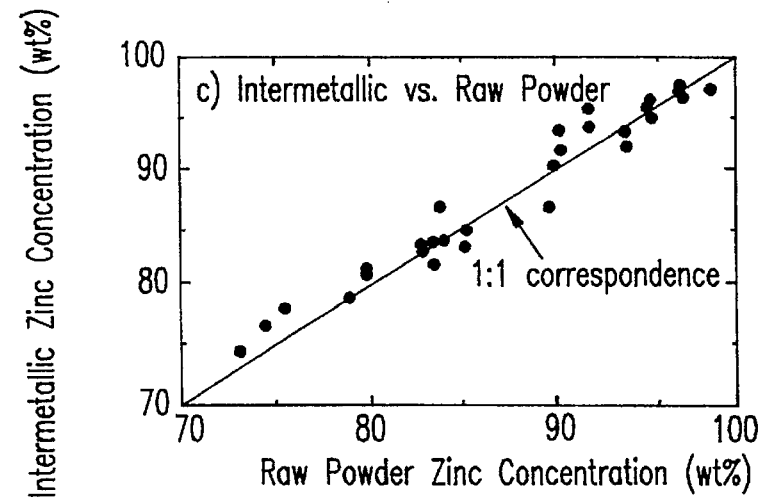
FIG. 3c is a graph corresponding to FIG. 2c, and is a graph comparing the measured zinc concentration determined using induction coupled plasma spectroscopy for intermetallics versus raw powders.

A comparison was made between the iron and zinc fractions, measured by ICP, in the same samples before and after sintering. These are shown in FIGS. 2c and 3c, respectively. It can be seen from the 1:1 correspondence line, which is a reasonable fit to the data, that ICP is measuring identical concentrations of iron and zinc before and after sintering. Therefore, based on FIGS. 2c and 3c, it can be concluded that ICP is not capable of measuring the absolute concentrations to the accuracy desired. In short, the technique underestimates iron concentration and overestimates zinc concentration in iron-zinc samples. However, ICP is able to accurately compare iron and zinc concentrations in different samples and is able to monitor possible changes in samples due to sintering and annealing.

B. Wet Chemical Titration

There are several titration techniques for determining the fraction of iron in materials. One such method uses a permanganate solution to oxidize the iron. However, it is important to choose a method whose titration end point is not affected by the presence of zinc. Unfortunately, the permanganate solution is not stable in air and since the effect of zinc on the solution is unknown, another oxidation-reduction standard with an end point that is not effected by the zinc in the solution was developed.

To accurately determine the fraction of iron in each sample, the following titration technique was performed three times on carefully measured masses of the same alloy. Samples were first reacted with 10–15 milliliters of concentrated hydrochloric acid and heated below the boiling point 20–40 minutes. Iron (II) and iron (III) formed as products according to the following equations:

$$2Fe+6H^+ \rightarrow 2Fe^{3+}+3H_2 \qquad \text{Eq. 1}$$

$$Fe+2H^+ \rightarrow Fe^{2+}+H_2 \qquad \text{Eq. 2}$$

The solution became yellow/orange due to the presence of iron(III). During the titration, iron(II) is oxidized to iron(III). Therefore, all of the iron(III) must initially be reduced to iron(II).

Tin(II)chloride can be used for reducing iron(III) to iron(II), as shown in Equation 3, and it changes the solution from yellow orange to nearly colorless.

$$Sn^{2+}+2Fe^{3+} \rightarrow Sn^{4+}+2Fe^{2+} \qquad \text{Eq. 3}$$

Serious errors can result if a large excess of tin(II)chloride is added because the tin(II) will also be oxidized during the titration to erroneously give high values of iron content. Therefore, tin(II)chloride was added dropwise to the yellow/orange solution until it became pale green or nearly colorless. A slight excess was added (2 drops) to ensure the complete reduction of iron(III). This slight excess of tin(II) was also oxidized so it would not interfere with the titration. A solution of mercury(II) chloride was added to oxidize the excess tin(II). If a slight excess of tin(II) was used, a white precipitate of mercury(I)chloride formed when the mercury (II)chloride was added. If too much tin(II)chloride was used to reduce the iron(III), a black precipitate of mercury formed when the solution of mercury(II)chloride was added. This difference in precipitates provides a method of checking whether the reduction of iron(III) has been performed correctly.

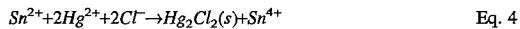
$$Sn^{2+}+2Hg^{2+}+2Cl^- \rightarrow Hg_2Cl_2(s)+Sn^{4+} \qquad \text{Eq. 4}$$

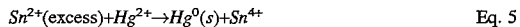
$$Sn^{2+}(excess)+Hg^{2+} \rightarrow Hg^0(s)+Sn^{4+} \qquad \text{Eq. 5}$$

If no white precipitate forms or if the precipitate is black upon addition of mercury(II)chloride solution, the sample should be discarded. Because the air slowly oxidizes iron (II), it is advantageous to reduce and titrate one sample before reducing the next sample, as was done in the analysis of the samples prepared according to Example 1.

Once reduction of iron (III) was complete, sulfuric and phosphoric acids were added to allow for a complete reaction during the titration and to cause the endpoint of the indicator to be sharper. The indicator used was barium diphenylamine sulfonate; however, other indicators may also be employed in the wet chemical method. The barium diphenylamine sulfonate was added to the solution and the solution was titrated with standardized potassium dichromate solution. The color change at the endpoint proceeded from a blue-green to grey to purple.

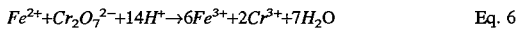
$$Fe^{2+}+Cr_2O_7^{2-}+14H^+ \rightarrow 6Fe^{3+}+2Cr^{3+}+7H_2O \qquad \text{Eq. 6}$$

The procedure described above was first used to standardize the titrant, potassium dichromate solution. A pure iron powder sample of known mass was used to measure the molarity of the titrant. Once the volume of the titrant needed to oxidize the iron had been measured, the molarity of the titrant was calculated according to Equation 7:

$$\text{Molarity}=(\text{mass of Fe powder})/(55.85 \times 6 \times \text{vol. of titrant}) \qquad \text{Eq. 7}$$

Depending on the amount of sample being analyzed, the molarity of the titrant ranged from 0.006670M to 0.01696M.

Once the titrant was standardized, the iron-zinc powders were tested. Sample sizes of the mixed raw powders and the iron-zinc intermetallics ranged from nearly 3 grams to 0.13 grams depending on the theoretical percentage of iron and the amount of the sample value for testing. The experimental percentage of iron was determined using the following calculations:

$$\text{Mass of Fe}=\text{molarity of titrant} \times 55.85 \times 6 \times \text{volume of titrant used} \qquad \text{Eq. 8}$$

$$\text{Fe(wt \%)}=(\text{mass of Fe(Eq.9)})/(\text{mass of sample}) \qquad \text{Eq. 9}$$

Figure 4:
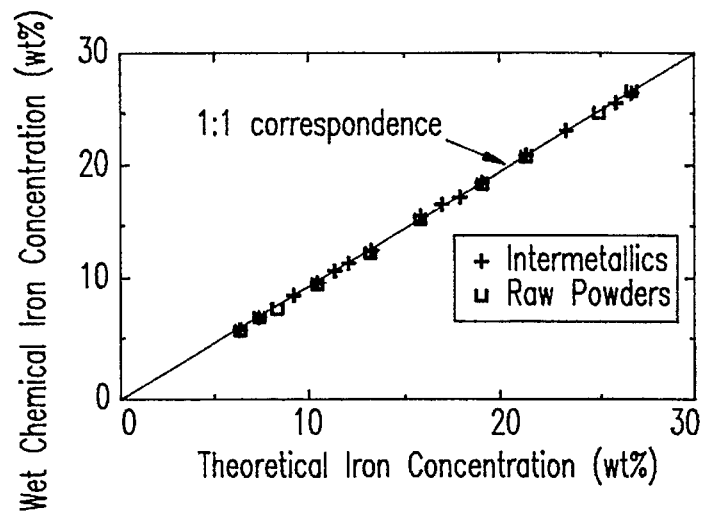
FIG. 4 is a graph of the wet chemical titration results showing the measured iron concentration compared to the expected values for the raw powders and intermetallics.
Figure 5A:
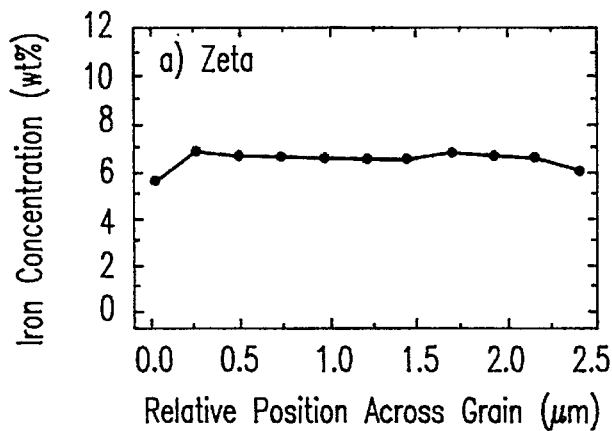
FIGS. 5a–d are STEM particle profiles of samples produced in each of the four main iron-zinc phases wherein the profile in FIG. 5a is for Zeta phase, the profile in FIG. 5b is for Delta phase, the profile in FIG. 5c is for Gamma-1 phase, and the profile in FIG. 5d is for Gamma phase.
Figure 5B:
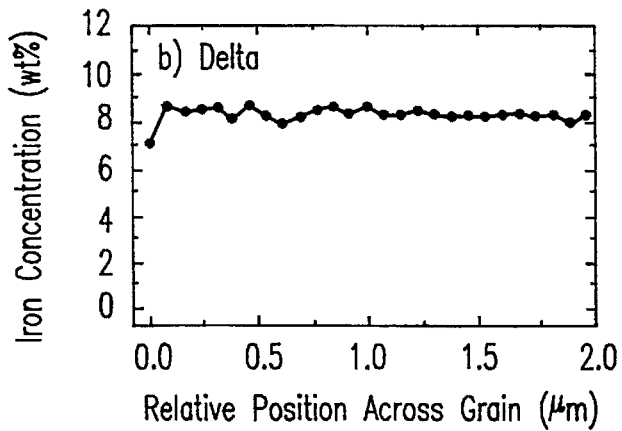
Figure 5C:
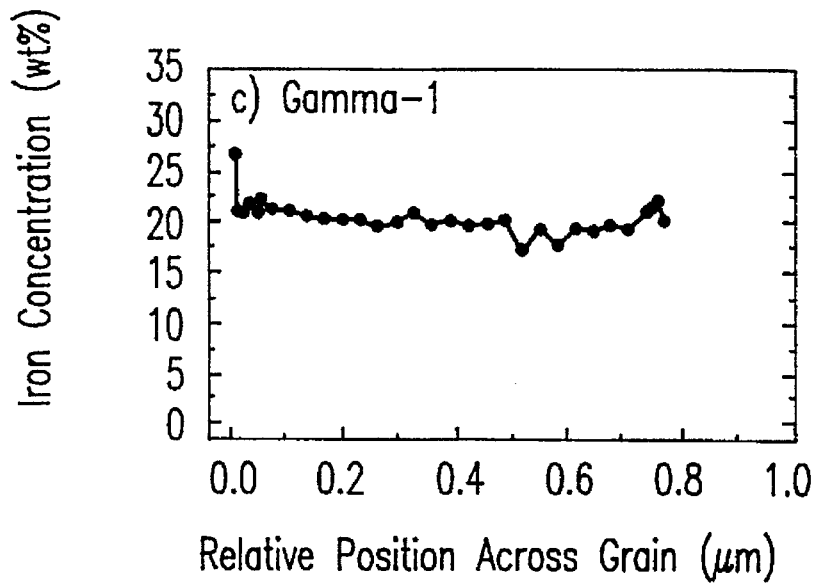
Figure 5D:
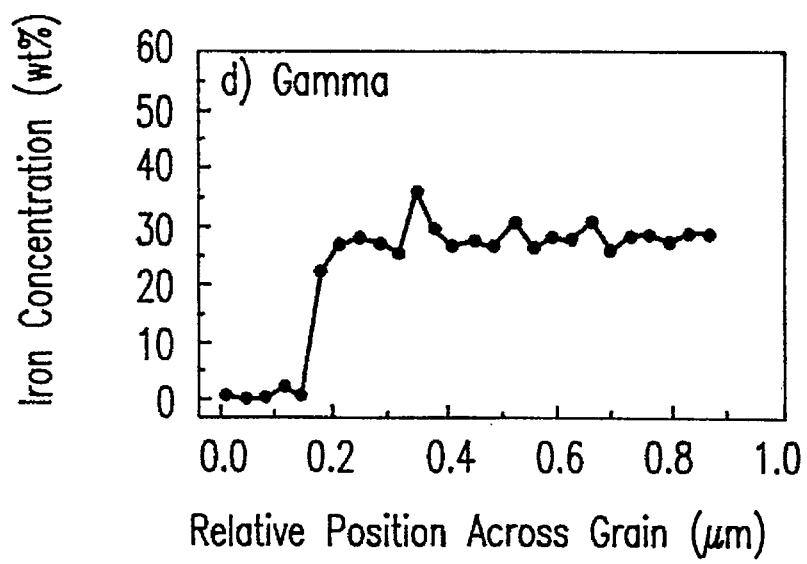

FIG. 4 shows the fraction of iron in the unsintered mixed powders and the fully sintered alloys prepared according to Example 1, as determined from wet chemical analysis, as described above, plotted as a function of the expected iron fraction. It can be seen that there is very good agreement between the two fractions. The wet chemical analysis technique establishes that the iron content in the samples was within 0.4 wt % of the expected value. In addition, the majority of the samples showed less than 0.1 wt % difference in the iron fraction between the unsintered raw powders and their corresponding fully sintered alloys. Furthermore, repeated wet chemical analyses, using the same sample, gave consistent iron concentrations within 0.1 wt % of each other.

C. Electron Microprobe

The homogeneity of each sample prepared in accordance with Example 1 was measured using an electron microprobe and scanning transmission electron microscope. The electron microprobe was used to measure the iron concentration in many particles of the same sample in order to monitor homogeneity between particles. An ETEC Autoprobe with a beryllium window, a Kevex Energy Dispersive System, and Krisel automation system was used to determine the iron concentration of many particles in the same sample. Typical probe volumes were about 10 cubic microns, thus allowing 1-2 probes to be made in most particles. Powders were mounted into standard 1" diameter plugs using a high quality epoxy resin. Each plug contained four separated powdered samples which had been finely sprinkled into the bottom of the mold which was then vacuum pumped before the epoxy was set and heated to 75° C. to speed the hardening. Samples were polished with diamond paste ranging from 600 μm down to 0.25 μm. Twelve samples, including the pure iron and zinc powders, were inserted into the microprobe chamber and analyzed sequentially. X-ray counts were collected for 200 seconds with a beam current of 215 pAmp, and data corrected to weight percent using ZAF correction. Both the iron and zinc peak positions were determined before each measurement in order to compensate for any electronic drift of the equipment. Pure, commercially produced iron and zinc standards as well as the iron and zinc powders used to make the iron-zinc alloys were used as calibration standards, since, prior to this invention, no Fe-Zn standards existed.

Table 1 shows the microprobe analysis of four samples, one from each of the main iron-zinc phases.

TABLE 1

Electron Microprobe Results of Samples Produced in Each of the Four Main Iron-Zinc Phases

| Sample | Point of Analysis | Normalized wt % Fe | Average wt % Fe and Stan. Dev. |
|---|---|---|---|
| Zeta | Part. #1-point#1 | 5.9 | Avg. wt % Fe = 5.86 |
|  | -point#2 | 5.94 | Stan. Dev. = 0.10 |
|  | -point#3 | 5.81 |  |
|  | -point#4 | 5.91 |  |
|  | Part. #2-point#1 | 5.71 |  |
|  | Part. #3-point#1 | 6.03 |  |
|  | Part. #4-point#1 | 5.78 |  |
|  | Part. #5-point#1 | 5.77 |  |
| Delta | Part. #1-point#1 | 8.20 | Avg. wt % Fe = 8.17 |
|  | -point#2 | 8.06 | Stand. Dev. = 0.08 |
|  | -point#3 | 8.11 |  |
|  | Part. #2-point#1 | 8.24 |  |
|  | Part. #3-point#1 | 8.14 |  |
|  | Part. #4-point#1 | 8.26 |  |
| Gamma-1 | Part. #1-point#1 | 20.72 | Avg. wt % Fe = 18.53 |
|  | -point#2 | 18.71 | Stand. Dev. = 1.28 |
|  | Part. #2-point#1 | 17.33 |  |
|  | Part. #3-point#1 | 20.20 |  |
|  | Part. #4-point#1 | 17.61 |  |
|  | Part. #5-point#1 | 17.57 |  |
|  | Part. #6-point#1 | 18.36 |  |
|  | Part. #8-point#1 | 17.78 |  |
| Gamma | Part. #1-point#1 | 23.72 | Avg. wt % Fe = 24.24 |
|  | -point#2 | 23.88 | Stand. Dev. = 0.30 |
|  | Part. #2-point#1 | 24.48 |  |
|  | Part. #3-point#1 | 24.20 |  |
|  | Part. #4-point#1 | 24.24 |  |
|  | Part. #5-point#1 | 24.34 |  |
|  | Part. #6-point#1 | 24.40 |  |
|  | Part. #7-point#1 | 24.63 |  |

It should be noted that, since pure iron and zinc powders were used for calibration, the absolute weight percentages are not considered to be accurate to better than 1 wt %. However, the variation in weight percentage from particle to particle, as indicated by the standard deviation, is a good measure of the homogeneity of the sample. As indicated in Table 1, several points within a particle were analyzed, as well as many different particles for each sample. The variation in the weight percentage of iron for each sample is small, thus indicating good sample homogeneity. In general the iron concentration in each alloy varies from the expected value by less than 0.5 wt %. Measurements of many particles of the same sample indicated an iron homogeneity greater than 98%.

D. Scanning Transmission Electron Microscopy

STEM was used to measure the iron concentration across any one particle to monitor the homogeneity on a more microscopic scale than is possible with the microprobe. In general, the STEM resolution was about 20 nm (probe volume is approximately 0.02 $\mu m^3$) and between 10–30 samplings were made across a particle at 30–60 nm intervals. Powder from each sample was embedded in the tip of a BEEM Capsule (size 00) with low vapor pressure epoxy. The epoxy plug was trimmed to a 20 μm pyramid and then 30–50 nm sections were cut dry using a Diatome 45° diamond knife sharpened to a 10 nm edge. The sections were attached on a collodion/Formvar/carbon coated grid, as described in Furdanowicz et al., *J. of Microscopy* 174:55 (1994), which was inserted into a Vacuum Generators HB501 STEM for microanalysis. The sample was tilted 10°–15° towards the detector to minimize absorption and shadowing by the grid bars. The STEM contained an AN 10,000 EDS system equipped with a 30 $mm^2$ windowless detector having a 1.48 eV resolution.

The composition profile across a particle was determined using a list of tracking points generated prior to automated aquisition. FIGS. 5a–d show the profiles of typical particles from a sample prepared in each of the four main iron-zinc phases. Since pure iron and zinc powders were used for calibration, the weight percentages are not considered to be as accurate as the variation in the weight percentage across a given particle. The weight percentage remains relatively constant across each particle demonstrating good homogeneity and sample diffusion. However, at the very edge of some of the particles, regions of high zinc, and therefore low iron concentration, were observed. This may be due to a very small amount of zinc oxide being present in the initial zinc powder.

The STEM analysis consistently gave iron concentrations within about 0.6 wt % of the expected value for the two low iron phases. However, for the two high iron phases, the iron concentration was only accurate to about 2 wt % of the expected value. Larger variations in iron homogeneity were also observed across individual particles using STEM. These ranged from 0.2 wt % to 2 wt % for the low and high iron phases respectively.

The separate identification of the four iron-zinc phases, and the determination of the fraction of each in a commercial galvaneal coating, can only be performed if the instrumentation is very accurately calibrated. The above procedures for producing an iron-zinc alloy which call for slow diffusion of zinc into iron, results in the formation of high purity, homogenous alloys, of the iron-zinc phases Zeta, Delta, Gamma-1 and Gamma. The technique allows standard alloys to be prepared at very precise positions on the Fe-Zn binary phase diagram. These standards, which are not positioned on a steel substrate, can then be used by commercial producers and users of galvanneal steel to calibrate instrumentation used to monitor the quality of galvaneal steel.

The standards produced by the above described process will be a grey powder before mounting. The powder can be supplied loose or mounted in a sample holder designed to fit into a calibration instrument. Sample sizes in a calibration instrument are typically 1"×1" square or 1" round or ½ round depending on the instrument. Quite a number of different holders can be used within the practice of this invention, and their design depends on the instrumentation to be calibrated. For example, the powder may be mounted in an epoxy plug and polished to expose the individual powder particles, or may be compressed and dry mounted if epoxy is not to be used.

While the invention has been described in terms of its preferred embodiments, those skilled in the art will recognize that the invention can be practiced with modification within the spirit and scope of the appended claims.

We claim:

1. A method of forming an iron-zinc alloy useful as a calibration standard, comprising the steps of:

mixing a known quantity of an iron powder together with a known quantity of a zinc powder to form a homogenous blend, wherein iron particles in said iron powder have a size of no larger than 20 µm, and wherein said iron powder has a purity of at least 97 wt % with no more than 0.5 wt % of any impurities in said iron powder being carbon or oxygen, and wherein said zinc powder has a purity of at least 97 wt % and zinc particles in said zinc powder have a size no larger than 100 µm;

compressing said homogenous blend to form a dense article including iron and zinc;

sintering said dense article for a first time and at a first temperature sufficient to cause interdiffusion of said zinc into said iron, but at a temperature less than 1000° C.;

powderizing a sintered material produced during said sintering step to produce an iron-zinc powder;

annealing said iron-zinc powder for a second time and at a second temperature sufficient to produce an annealed iron-zinc alloy;

determining the micro structure of said iron-zinc alloy; and determining a percentage of iron and a percentage of zinc in said iron-zinc alloy from said known quantity of iron powder and said known quantity of zinc powder used in said mixing step.

2. The method of claim 1 wherein said mixing step includes the step of selecting said iron particles in said iron powder to be no larger than 10 µm.

3. The method of claim 1 wherein said mixing step includes the step of selecting said iron particles in said iron powder to be no larger than 5 µm.

4. The method of claim 1 wherein said first time and said first temperature used in said sintering step are approximately the same as said second time and said second temperature used in said annealing step.

5. The method of claim 1 wherein said sintering step is performed at a temperature of less than 800° C.

6. The method of claim 1 wherein said first time in said sintering step is 4–10 days.

7. The method of claim 1 wherein said mixing step includes the step of selecting said known quantity of iron powder to constitute 4–30 wt % of said homogenous blend and said known quantity of zinc powder to consitute 70–96 wt % of said homogenous blend.

8. The method of claim 1 wherein said step of determining said percentage includes the steps of:

converting Fe to Fe(II);

reducing Fe(III) to Fe(II);

oxidizing Fe(II) to Fe(III) using an oxidizing agent as a titrant;

determining a molarity of said titrant used in said oxidizing step; and calculating a wt % of Fe from said molarity of said titrant.

9. The method of claim 8 wherein said reducing step utilizes stannous chloride.

10. An iron-zinc alloy calibration standard having an iron concentration between 4 and 27 wt %, made by the process of mixing a known quantity of an iron powder together with a known quantity of a zinc powder to form a homogenous blend, wherein iron particles in said iron powder have a size of no larger than 20 µm, and wherein said iron powder has a purity of at least 97 wt % with no more than 0.5 wt % of any impurities in said iron powder being carbon or oxygen, and wherein said zinc powder has a purity of at least 97 wt % and zinc particles in said zinc powder have a size no larger than 100 µm;

compressing said homogenous blend to form a dense article including iron and zinc;

sintering said dense article for a first time and at a first temperature sufficient to cause interdiffusion of said zinc into said iron, but at a temperature less than 1000° C.;

powderizing a sintered material produced during said sintering step to produce an iron-zinc powder;

annealing said iron-zinc powder for a second time and at a second temperature sufficient to produce an annealed iron-zinc alloy.

11. The iron-zinc alloy calibration standard of claim 10 wherein said annealed iron-zinc alloy is homogenous to greater than 98%.

12. The iron-zinc alloy calibration standard of claim 10 wherein said annealed iron-zinc alloy is greater than 99.5 wt % pure.

13. The iron-zinc alloy calibration standard of claim 10 wherein said iron-zinc alloy is a powder.

14. The iron-zinc alloy calibration standard of claim 10 further comprising a sample holder for said iron-zinc alloy.

\* \* \* \* \*